US005619775A

United States Patent [19]
Klinck

[11] Patent Number: 5,619,775
[45] Date of Patent: Apr. 15, 1997

[54] SAFETY LATCH FOR A REMOVABLE CLIP FOR A COLOSTOMY BAG

[76] Inventor: Barry W. Klinck, 4680 Brandywine Dr., Baco Raton, Fla. 33487

[21] Appl. No.: 583,950

[22] Filed: Jan. 11, 1996

Related U.S. Application Data

[63] Continuation-in-part of Ser. No. 26,488, Jul. 29, 1994, abandoned.

[51] Int. Cl.$^6$ .................................................. B65D 77/10
[52] U.S. Cl. ........................................ 24/30.5 R; 24/543
[58] Field of Search ............................ 24/30.5 R, 30.5 P, 24/17 B, 482, 542–544, 517, 518, 543

[56] References Cited

U.S. PATENT DOCUMENTS

| 285,908 | 10/1883 | Ludington . |
| 1,781,709 | 11/1930 | Spear ........................................ 24/544 |
| 2,087,786 | 7/1937 | Straus ..................................... 24/217 B |
| 3,036,506 | 5/1962 | Andresen, Jr. ................... 24/30.5 R X |
| 3,523,534 | 8/1970 | Nolan . |
| 4,887,335 | 12/1989 | Folkmar . |
| 4,983,172 | 1/1991 | Steer et al. . |
| 5,050,272 | 9/1991 | Robinson et al. . |
| 5,125,133 | 6/1992 | Morrison . |
| 5,379,489 | 1/1995 | Delk et al. . |
| 5,428,871 | 7/1995 | Iosif . |

FOREIGN PATENT DOCUMENTS 921619  5/1947  France ..................................... 24/482

Primary Examiner—James R. Brittain
Attorney, Agent, or Firm—Malin, Haley, DiMaggio & Crosby, PA

[57] ABSTRACT

A safety latch for a clip that is conventionally used to sealably close the opening in an ostomy or colostomy bag. The purpose of the safety latch is to prevent the accidental disengagement of the clip arms when engaged to the colostomy bag opening, forming a seal therein. The safety latch includes a resilient latch that, when engaged between the arms of the clip, is in a stretched condition, putting the clip arms in tension. The safety latch can be removed manually by additional stretching of the resilient member that holds the arms together.

6 Claims, 3 Drawing Sheets

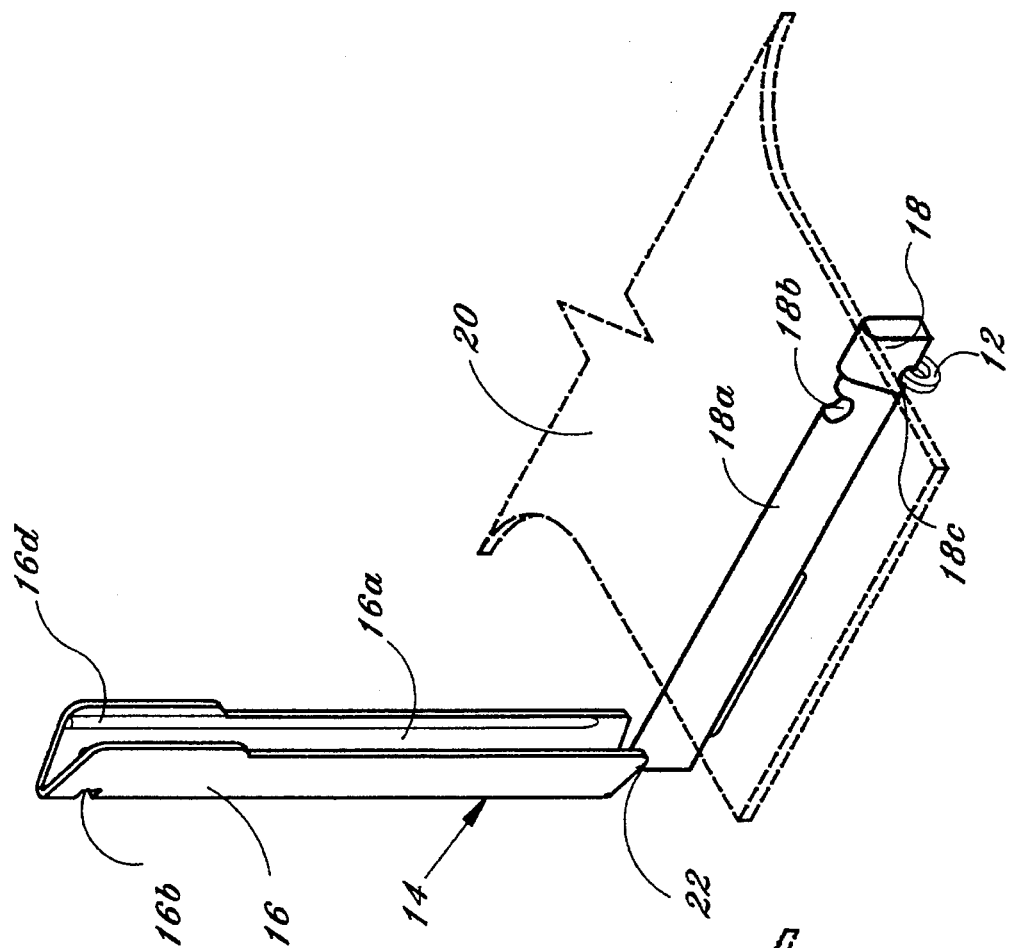
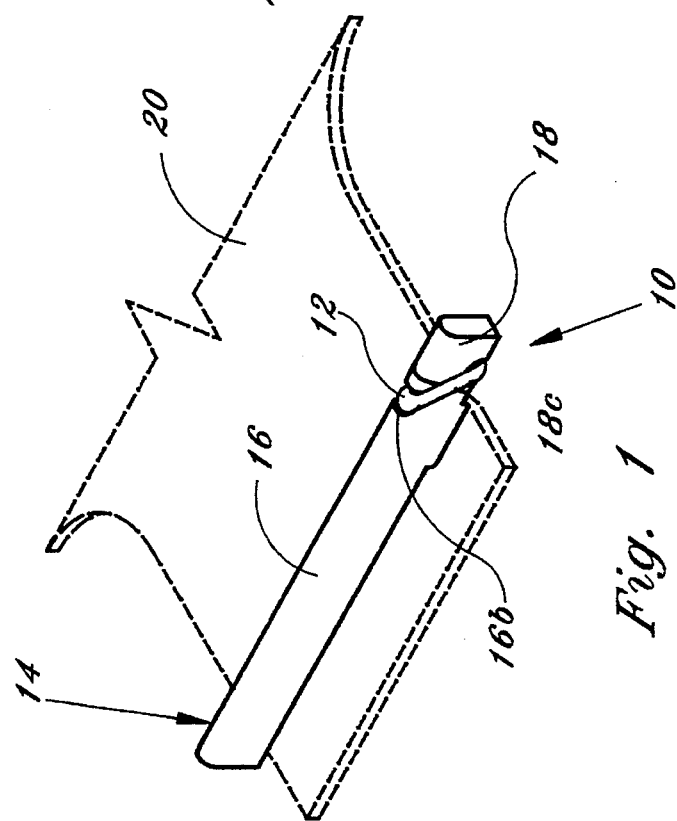

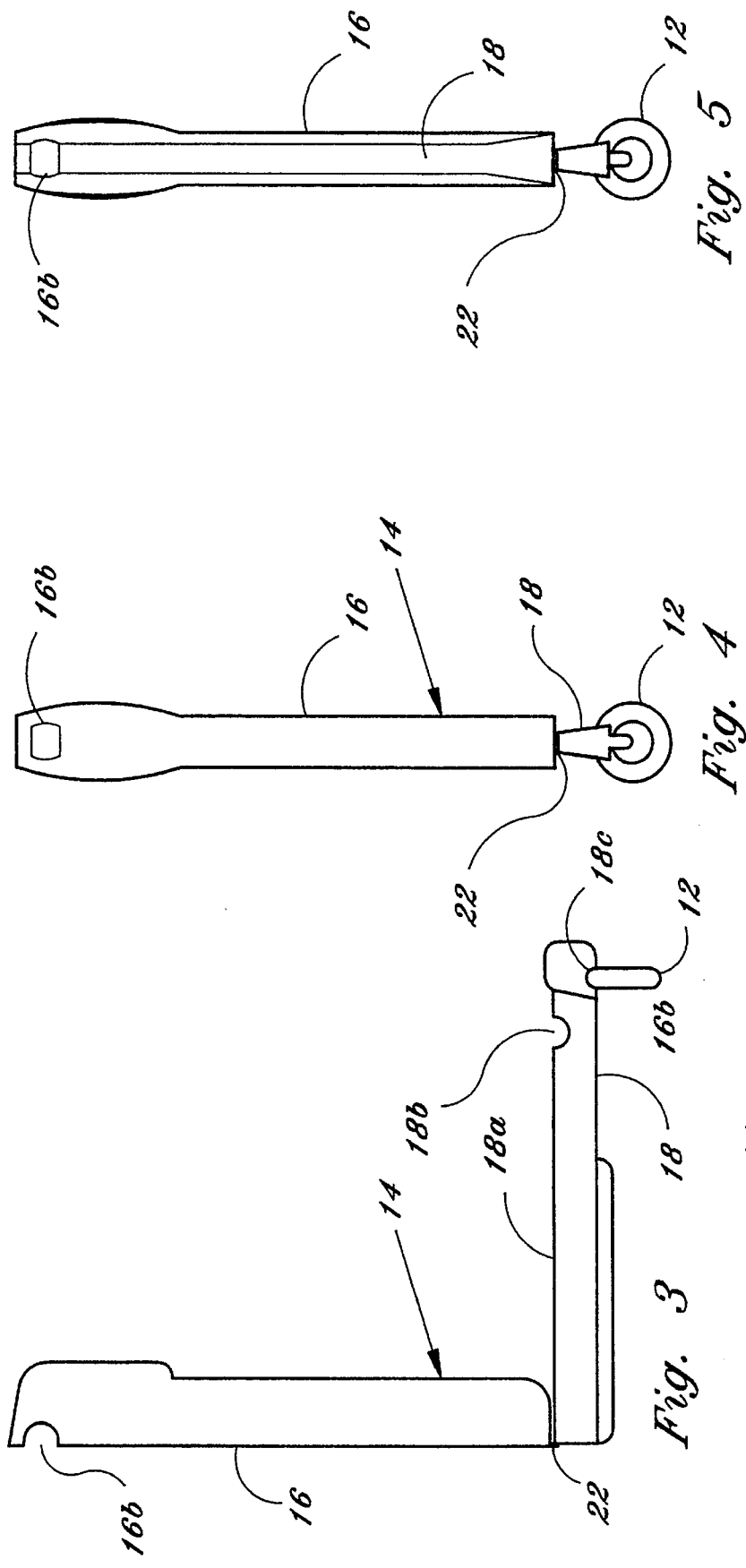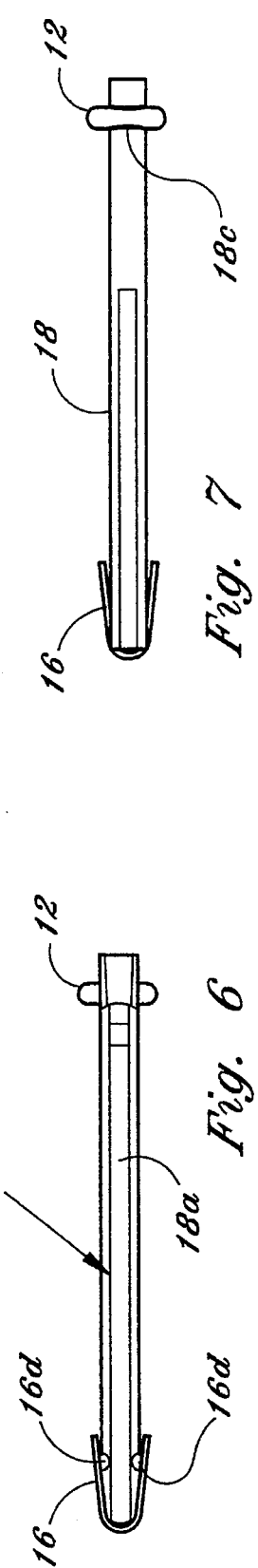

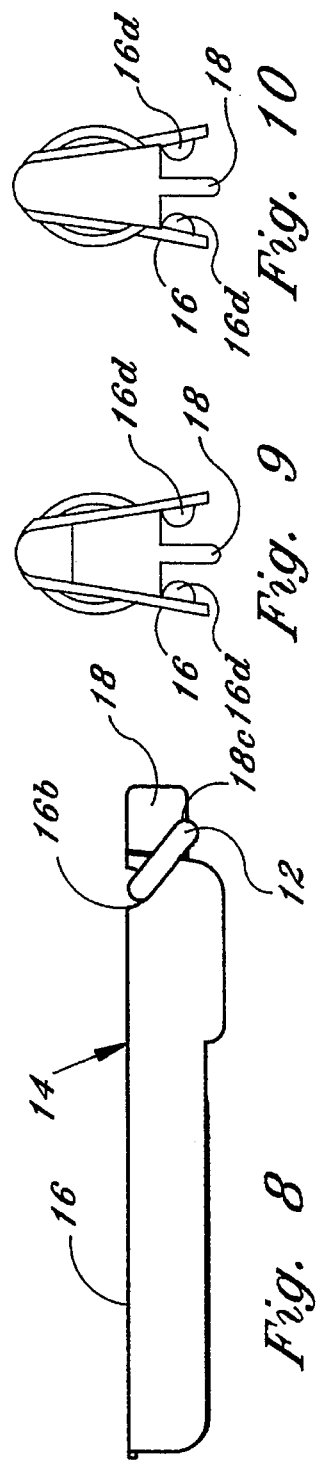
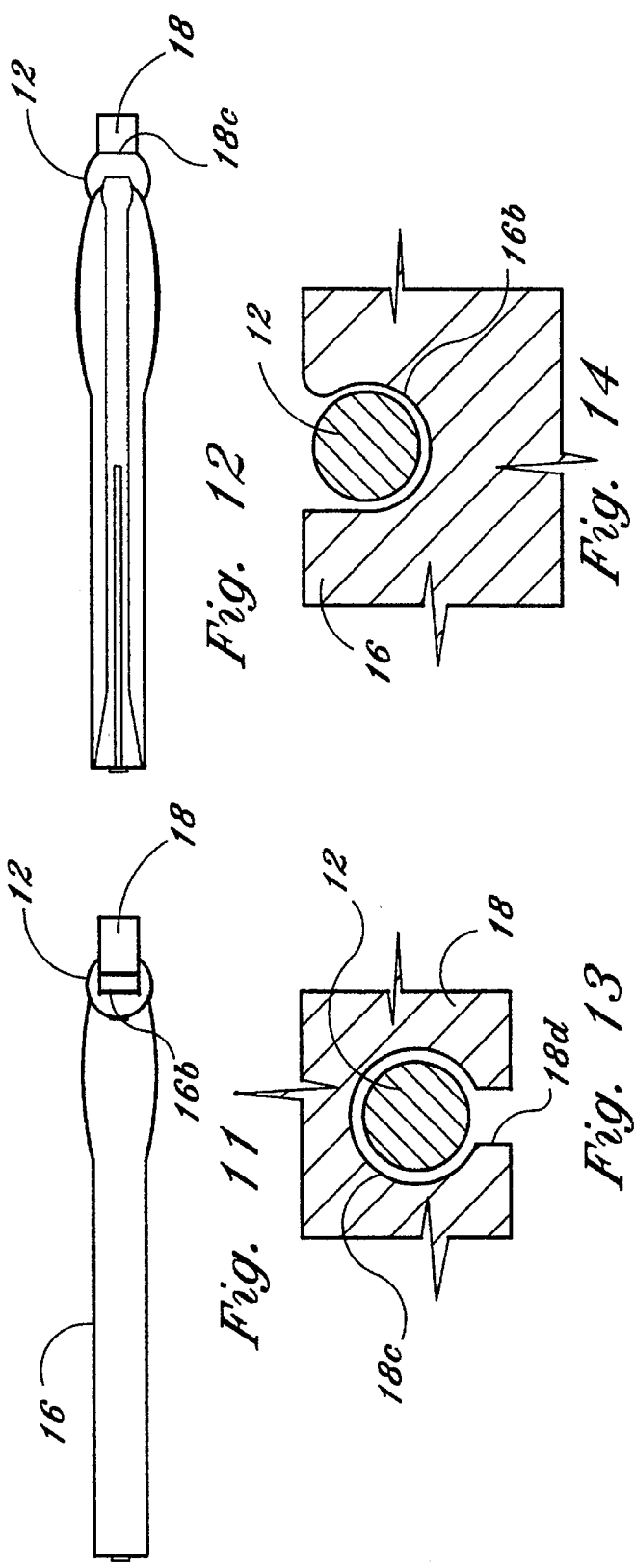

SAFETY LATCH FOR A REMOVABLE CLIP FOR A COLOSTOMY BAG

This application is a Continuation-In-Part of U.S. application Ser. No. 29/026,488 filed on Jul. 29, 1994 abandoned.

BACKGROUND OF THE INVENTION

1. Field of the Invention

This invention relates generally to ostomy and colostomy bag clips which are removable and that form seals on openings in a colostomy bag and specifically, to a safety latch for the ostomy bag closure clip to prevent accidental disengagement of the clip from the bag.

2. Description of the Prior Art

Colostomy and ostomy bags are used with patients to allow for disposal of bodily waste which collects in the ostomy bag. The bag typically has a lower opening end which has traditionally been sealed by a clip. When the bag is to be emptied, the clip is manually removed, allowing the bag contents to be disposed of.

Because of the physical demands on such clips to only be released when required, it is imperative that the clip remain firmly in place, regardless of the movements of the user, at all times, until manually disengaged by the user.

The prior art shows a plethora of plastic clips, typically having two or more arms or branches hinged together by a unitary plastic connection. Typically, the devices are hinged in a flexible manner which allows them to be bent and joined together with a protuberance that overrides a projecting surface for locking the clip in place. U.S. Pat. No. 5,125,133, issued Jun. 30, 1992 to Morrison, shows an ostomy pouch clamp with a hinge supplementing guide blade which allows for the pouch opening to be sealed by the guide blade action and which allows the clamp to be resiliently locked in place. U.S. Pat. No. 3,523,534, issued Aug. 11, 1970 to Nolan, shows a closure for a drainage pouch. U.S. Pat. No. 5,379,489, issued Jan. 10, 1995 to Delk et al., shows a bag closure clamp with a hinge supplementing complementary cam surface. This also provides for a resiliently disengageable latch or lock to keep the hinge engaged except when the locking pin is pressed physically and flexed. U.S. Pat. No. 4,887,335, issued Dec. 19, 1989 to Folkmur, shows a closure which is a plastic clamp or clip for closing plastic bags and the like. U.S. Pat. No. 5,428,871, issued Jul. 4, 1995 to Iosif, shows a clamp for elastomeric bags which has a locking pin that engages a resilient opening.

U.S. Pat. No. 4,983,172, issued Jan. 8, 1991 to Steer et al., shows a clip for a drainable ostomy pouch. As described herein, ostomy pouch and colostomy bag are used interchangeably. The clip for a drainable ostomy pouch in Steer et al., U.S. Pat. No. 4,983,172 shows a single, unitary clip made of a plastic that can be bent with a pair of branches engaged together by a resilient catch. The drawback for the clip shown in Steer et al. is that it can be accidentally opened by certain movements of the user. Such accidental opening obviously can be extremely embarrassing for the user. While the clip itself functions adequately and does maintain a seal of the bag's lower opening when engaged, accidental disengagement is unacceptable.

The purpose of the present invention is to provide a safety latch or safety lock for a clip, such as that shown in Steer et al., to absolutely prevent any type of accidental disengagement of the clip arms, while still making the deliberate disengagement of the clip relatively simple manually in order to empty the bag. With the safety latch in place, it is physically impossible for the clip to become accidentally disengaged. The safety latch, in accordance with the present invention, is non-complex in design and economical in the overall manufacture.

Present day ostomy and colostomy bag clips are sadly deficient in their holding power. Because these clips are unitarily formed often of plastic or plastic-like materials with a flexible hinge connecting the clip arms most clips have one or more protrusions which act to fit into a slot plastic to plastic that is manually overridden when the clip is disengaged. Clip separation and accidental release and opening of the clips is quite a common event. Users of the ostomy and colostomy bags often have to empty the bags several times a day increasing the probability of accidental disengagement. Most often, however, the problem is that the catch integrally formed in the conventional clip does not have the type of holding power necessary to insure and guarantee a secure lock. This is because if it was made that tight it would be impossible manually to override the catch. The present invention overcomes these problems by providing a foolproof safety latch that cannot come apart accidentally.

SUMMARY OF THE INVENTION

A safety latch for preventing the accidental disengagement of an ostomy bag clip, comprising a resilient ring, said ring having a predetermined internal diameter and being constructed of a resilient material that allows it to return after stretching to its original diameter.

The ostomy bag clip includes first and second branches which are unitarily formed together through the use of a unitary flexible hinge and includes a locking channel in one branch that engages the ostomy bag opening to form a closure when the clip branches are engaged together. One of the branch hinges disposed on its outer surface away from the hinge portion includes an arcuate recess angularly disposed with a tapered wall in the direction of the branch free end.

The other branch of the clip includes a retaining circular aperture that engages one portion of the latching ring, providing for a permanent mount or attachment of the ring to the branch arm. The branch arm that retains the ring permanently extends in length beyond the opposing branch arm which contains a channel to receive the blade-like effect of the other branch in the engaged position.

The ring receiving, tapered recess on the branch channel arm is strategically located near the end of the branch arm and the ring is sized such that in the engaged position, one can manually move the ring portion into the tapered recess, which firmly locks the clip branches together in the sealing position for the ostomy bag. Because the recess is tapered upwardly, pointing towards the free end of the clip's branches, in order to remove the ring manually to disengage the clip, the ring must be stretched upward over center and over the recessed arm that is angled in order to remove the ring to allow the clip to be disengaged. Thus, the ring inside diameter is strategically sized to fit snugly and totally between its permanent mounting annular opening and the tapered recess to insure that the clip branch arms are held firmly in place in the natural position.

To operate the clip with the safety latch when the clip is in the disengaged or open position, both branch arms are rotated in hinge-like fashion so that the blade of one branch arm engages the channel of the other branch arm with the bag end opening therebetween, thereby sealing the bag. The clip may include its conventional resilient fastener which merely requires that the channel opening along one portion be spread apart, allowing the other blade arm to be released. With the safety latch of the present invention, however, the resilient ring is manually disposed into the locking recess in the channel arm, firmly locking the clip in place.

The only way that the clip can now be disengaged so that the branch arms can be separated, allowing the bag to be opened, is for the resilient ring to be manually forced and stretched about one wall of the recess, and due to the recess angle, a deliberate, manual engagement is required.

In the open position, the retaining annular opening in the blade arm will keep the ring attached to the blade arm when the clip has been disengaged and the bag opening used to empty the bag. The manual dexterity required to either engage or disengage the safety latch through manipulation of the ring is quite simple and does not require any extra dexterity or strength. In the preferred embodiment, the safety latch is a small, rubber O-ring, wherein the tubular diameter is selected for proper adaptation to the clip size and the inside diameter of the O-ring itself (not the body tubular portion) is selected to fit snugly between each recessed portion on each arm when the pin is firmly engaged in the locking position. The resiliency of the O-ring is selected so that it can stretch to a distance greater than its internal diameter to allow it to be manipulated manually over and around the wall of the recess in the blade arm. The resiliency of the O-ring allows it to return snugly in the locked position so that the clip will not be allowed to open. The branch arm body having the channel that receives the latching recess with the recess being angled such that the safety latch has to be resiliently pulled in its own plane in order to get around the upper portion of the safety latch receiving recess, such that the upper portion of the safety latch recess extends beyond the end portion of the resilient O-ring when it is in place, locking the branches together.

The plane of the safety latch O-ring is at a distinctive angle when in the latched or safety lock position relative to the longitudinal axis of the clip branches when they are engaged together. Although the safety latch could work if the plane of the resilient ring were perpendicular to the longitudinal axis of the arms or branches of the clip when they are engaged in the locked position, it is believed that the angle requires that the resilient latch be moved in such a way that it enhances the distance required and counteracts the tendency of the hinge to move in an arcuate direction or tangential direction.

It is an object of this invention to provide an improved clip for an ostomy or colostomy bag opening that is removable, that prevents any accidental disengagement of the sealing clip of the bag.

It is another object of this invention to provide an improved safety latch for an ostomy bag clip that prevents accidental disengagement of the clip, but can be easily manually removed when required.

And yet another object of this invention is to provide an improved ostomy bag clip having a safety latch or safety lock that can only be disengaged by deliberate manual intervention of the user, and that is non-complex in operation and economical to manufacture.

In accordance with these and other objects which will become apparent hereinafter, the instant invention will now be described with particular reference to the accompanying drawings.

BRIEF DESCRIPTION OF THE DRAWINGS

FIG. 1 is a perspective view of the invention in the clipped mode and showing a segment of an ostomy pouch in phantom.

FIG. 2 is a perspective view of the invention in the unclipped mode showing an O-ring latch in engaged with an arcuate recess on an upper branch of the invention and the ostomy pouch in phantom.

FIG. 3 is a front elevational view of the invention in the unclipped mode showing the O-ring latch attached within a second arcuate recess on a lower side of the invention as shown in FIG. 1.

FIG. 4 is a left-end elevational view of the invention in the unclipped status as shown in FIG. 2.

FIG. 5 is a right-end elevational view of the invention in the unclipped status as shown in FIG. 2.

FIG. 6 is a top plan view of the invention in the unclipped status as shown in FIG. 2.

FIG. 7 is a bottom plan view of the invention in the unclipped status as shown in FIG. 2.

FIG. 8 is a side elevational view of the invention in the clipped status showing the O-ring latch engaging the first arcuate recess on the upper side of the invention as shown in FIG. 2.

FIG. 9 is a left-end elevational view of the invention in the clipped status as shown in FIG. 1.

FIG. 10 is a right-end elevational view of the invention in the clipped status as shown in FIG. 1.

FIG. 11 is a top plan view of the invention in the clipped status as shown in FIG. 1.

FIG. 12 is a bottom plan view of the invention in the clipped status as shown in FIG. 1.

FIG. 13 shows a cut away partial side elevational view and cross section of the keyhole aperture that retains the O-ring within branch 18 so that it is very difficult to be removed.

FIG. 14 shows a partial cut away side elevational view and cross section of a portion of the branch arm and the recessed area for retaining the O-ring latch.

DESCRIPTION OF THE PREFERRED EMBODIMENTS

Referring now to the drawings and in particular FIGS. 1 and 2, the present invention is shown generally at 10, and includes an ostomy bag portion 20 (shown dotted) and an ostomy bag closure clip 14 shown in the fastened position, including resilient O-ring 12 which locks the clip branch members 16 and 18 firmly together. The position shown in FIG. 1 is with the safety latch in position to keep the clip closed.

FIG. 2 shows the same clip 14 in the unlocked position, again with 20 representing a portion of an ostomy bag, or colostomy bag, or any other resilient bag that has an opening that can be sealed by clip 14. Clip 14 includes a first branch 16 that has a channel 16a, an O-ring receiving recess 16b near the free end of branch 16, and a flexible hinge 22 that connects branch 16 to branch blade 18. The blade portion 18a fits along channel 16a to seal and lock the material of the colostomy bag between the branches firmly to prevent any leakage of moisture or materials from the bag in the closed position, as shown in FIG. 1. The blade or branch 18 includes a circular recess 18c that is greater than a half-circle that permanently retains a resilient rubber O-ring 12 connecting it permanently to branch 18. O-ring 12 can rotate, but a substantial portion of the aperture 18c surrounds the outer circumference of the O-ring in one location to retain the O-ring attachably to branch 18. Branch 18 also has a small recess 18b that coincides longitudinally with the recess in branch 16, designated as 16b, so that when branch 18 is engaged with branch 16, the O-ring can be stretched into recess 16b and 18b, as described below.

FIG. 2 shows the O-ring which is circular, having a circular internal diameter and a circular outside diameter, along with its own circular body. As shown in FIG. 1, the distance from the bottom of recess 18c to the bottom of recess 16b is such that it is greater than the internal diameter of O-ring 12 in a relaxed state, as shown in FIG. 2. This allows, because of the elastic and resilient nature of the rubber or artificial rubber used in the construction of O-ring 12, in the stretched position O-ring 12 maintains a resilient force holding branch 16 against branch 18. The angular relationship with respect to the longitudinal axis of branch 16 and branch 18 in the locked position shown in FIG. 1 is such to resist further the hinge motion of the clip 14, that is the plane form between recess 16b and recess 18c relative to the longitudinal axis of branch 16 and branch 18 in the locked position shown in FIG. 1.

FIG. 3 shows branch 16 unitarily formed and connected to branch 18 by a flexible hinge 22. This is the conventional construction of the clip. Applicant's invention includes the addition of a resilient O-ring receiving arcuate recess 16a disposed adjacent the free end of branch 16 and resilient O-ring receiving recess 18b which aligns and coincides with recess 16a of branch 16 when branch arm 16 is locked and receives blade 18a and branch 18 in the channel within branch 16. The O-ring 12 is shown attached to branch 18 in a circular recess 18c, the perimeter of which is greater than the semicircular distance around the O-ring body itself. Thus, a small opening, much smaller than the circular diameter of recess 18, is presented where the O-ring 12 is firmly positioned within when the device is made at the factory, when the O-ring is joined to the clip 14.

FIG. 4 shows a left-hand view of the position of the clip 14 as shown in FIG. 3.

FIG. 5 shows a right-hand view of the position of the clip shown in FIG. 3, which shows the O-ring receiving recess 16b near the end of branch 16.

FIG. 6 shows that the clip 14, and in particular branch 16 near the free end, has a pair of raised protrusions 16d on the inside of the channel which act as a catch against the outside back of branch 18 in the locked position (as shown in FIG. 1) so that the channel formed in 16 is resilient enough so that the protrusions 16d are spread apart when the clip branch 16 is disengaged manually from catch formed by 16d protrusions. However, Applicant has found that that catch, which is conventional, is not sufficient to prevent accidental release of branch 16 from branch 18. The O-ring 12, in conjunction with recess 16b and recess 18b, firmly holds branch 16 against branch 18 unless the O-ring is stretched manually to disengage it from the branch recesses 16b and 18b.

FIG. 7 shows the O-ring 12 firmly engaged in circular recess 18c, the opening of which is smaller than the diameter of the O-ring body (the tubular body of the O-ring).

FIG. 8 shows the safety latch for clip 14 formed by the resilient O-ring 12, which in the position shown in FIG. 8 is stretched beyond its normal, relaxed inside diameter between recess 16b and recess 18c, safely locking together branch 16 into branch 18. In order to disengage the clip, the resilient O-ring, any radial movement of branch 18 away from branch 16 is clearly resisted and prevented by the stretched O-ring 12, and enhanced by the angle of the O-ring relative to the longitudinal axis of arm 18 and branch 16.

FIG. 9 shows the catch formed by protrusions 16d in the flexible channel in branch 16 when it engages branch 18 that resists opening. However, because of the resilient nature of channel 16a in branch 16, the conventional catch is very easy to disengage with very little force required to overcome the catch 16d making the clips easier to operate for the user but much more likely to separate or accidently open. If catch 16d were made to require extreme force to open, manual use would be difficult.

FIG. 10 shows the opposite end of the device in elevation shown in FIG. 8.

FIG. 11 shows the top view with the O-ring 12 engaged in recess 16b with branch 16 firmly engaged and locked to branch 18 by O-ring 12.

FIG. 12 shows the O-ring as it is retained by recess 18c in branch 18, where the opening 18c outside of the branch arm is greatly smaller than the tubular diameter of the O-ring body itself, thereby firmly holding and attaching the O-ring 12 to branch 18 at all times.

To operate the present invention, referring to FIG. 8, the safety latch is shown engaged by O-ring 12 being in a stretched, fixed position, having a portion in recess 16b and another portion where it is permanently attached to branch 18 in aperture 18c. To disengage the safety latch, the O-ring 12 is manually grasped and pushed upwardly over the top of branch end 16, freeing branch 16 and allowing the O-ring to be removed from recess 16b. The different positions of locked and unlocked clip are shown also in FIGS. 1 and 2.

It is clearly seen that unless the O-ring is stretched manually out of the recess 16b, the clip itself is firmly locked in place so that it cannot become accidentally dislodged from the ostomy bag or any other bag opening.

Although a rubber or artificial rubber, resilient or elastic O-ring has been disclosed, a suitable resilient plastic O-ring could also be utilized. It is important that the recessed branch 16b be of sufficient arcuate size to receive the entire cross section portion of the O-ring. It is likewise important that the distance between the perimeter of the recess 16b as it faces the perimeter of recess 18c exceed the natural inside diameter of the O-ring in its resting position when not stretched, so that the O-ring is in a stretched tension in the locked position shown in FIG. 8. It is also important to keep the O-ring permanently attached to branch 18 by insuring that the aperture holding the O-ring has a circumference that is almost equal to the circumference of the tubular body of the O-ring, but still with sufficient opening to allow the O-ring to be installed initially.

FIG. 13 shows the arcuate aperture 18c with a passage 18d that is much smaller than the diameter of arcuate aperture 18c and much smaller than the diameter of the O-ring 12 to insure that at all times the O-ring 12 remains attached or fixed to the clip and in particular to branch 18. This insures that the user, when opening or closing the clip and the contents of the ostomy bag, does not accidently lose the O-ring or have it spring off of the device at the worse possible time.

In summary, present day clips which are usually solid piece plastics having a flexible joint have been used for ostomy and colostomy bag sealable closures allowing the bags to be periodically emptied which can be up to several times a day. The great deficiency in these clips is that the catches which are provided which are typically integral protrusions which overlap the opposing arm of the clip are very easily accidentally opened by the slightest pressure that might try to separate the arms of the clip. To have the clip which is located at the bottom of the bag which has an opening come off is a disastrous result but not uncommon with clips found in conventional ostomy and colostomy bags. The purpose of this invention is to insure with nothing left to chance that the clip body cannot separate with the safety latch in place avoiding extremely embarrassing situations for the user. Thus, in addition to the catch found in conventional clips, with the addition of the safety latch, the user can feel comfortable and secure in the day to day use of the bag clips. In addition, with the present invention, the O-ring cannot become dislodged from the body of the clip, another important feature for users. The present invention thus solves the safety latch problem and insures that the safety latch is always available and does not separate from the clip body.

Referring now to FIG. 14, the recessed slot 16b is shown in body 16 that receives the O-ring latch 12 which is in tension or stretched into position. Note the arrow showing the direction of stretch in the preferred embodiment which requires that in order to release branch 16 the O-ring must be additionally stretched up and over the upper part of the recessed 16b. This configuration where the recess itself overlaps a portion of the O-ring vertically especially away from the direction of tension or stretch of the O-ring completely insures the security of the safety latch. Only manual intervention as stretching in a direction parallel to the arrow overriding the top portion of recess 16b will release the O-ring latch.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A safety latch for an ostomy pouch clip to prevent accidental disengagement of the clip, comprising:

an ostomy bag clip body, unitarily formed, having a first branch and a second branch;

a flexible hinge member connecting said first branch to said second branch, allowing said first branch to move pivotally relative to said second branch;

said clip body first branch having a free end and an opposite end connected to said hinge member, said second branch of said clip body having a free end and an opposite end connected to said hinge member, said first branch having a recessed area near its free end and said second branch having a recessed area near its free end; and a resilient fastener, said resilient fastener having a first state of a given size and a second, stretched state of a second size, said resilient fastener connected to said first branch recessed area and within said second branch recessed area in a stretched state, locking said first branch against said second branch when they are together;

said clip body second branch recessed area including a retaining aperture, said second branch recessed area retaining aperture having a circumference less than a complete circle (360 degrees), but greater than a semicircle (180 degrees), said resilient fastener having an exterior circumference with a diameter that approximates the diameter of said second branch retaining aperture;

whereby said resilient fastener can be manually removed from said first branch recessed portion, allowing said first branch to be separated from said second branch, said resilient fastener is held and connected to said second branch member.

2. A safety latch as in claim 1, wherein:

said resilient fastener is a resilient O-ring having a predetermined inside diameter that at rest, in an unstretched or deformed state, is smaller than the distance between said first branch recessed area and said second branch recessed area.

3. A safety latch as in claim 1, wherein:

said first branch includes a channel sized to receive said second branch when said clip is in an engaged position.

4. A safety latch as in claim 3, wherein:

said first branch includes a resilient catch for engaging said second branch.

5. A safety latch for an ostomy or colostomy bag opening clip that sealably engages and closes the bag opening when engaged thereto, said safety latch for said clip comprising:

a clip body having a first arm and a second arm integrally formed and hinged together by a flexible hinge, having a first open position and a second position where said first arm and second arm are engaged together, forming a seal across a colostomy or ostomy bag opening in the engaged position;

said first arm and said second arm each including a retaining aperture, each of said first arm and said second arm retaining apertures having a circumference less than a complete circle of 360 degrees, but greater than a semicircle of 180 degrees; and a resilient latch member connectable to said first arm and said second arm at said first arm and said second arm retaining apertures in a stretched condition under tension to prevent the disengagement of said first arm from said second arm when engaged across a colostomy bag opening, and manually removable by additional stretching from said first arm and said second arm to allow the disengagement of said first arm from said second arm.

6. A safety latch as in claim 5, wherein:

said resilient latch member is an O-ring having a predetermined inside diameter that, when engaged between said first arm and said second arm, the inside diameter is in a non-circular, stretched length.

* * * * *